United States Patent [19]

Gores et al.

[11] Patent Number: 4,544,354

[45] Date of Patent: Oct. 1, 1985

[54] ANTERIORLY BRIDGED DENTAL TRAYS

[76] Inventors: Kenneth W. Gores, 1026 - 112th St. N.E., Bellevue, Wash. 98004; Carolyn C. Gores, 827 Lake St., Kirkland, Wash. 98023

[21] Appl. No.: 652,636

[22] Filed: Sep. 21, 1984

[51] Int. Cl.$^4$ .............................................. A61C 9/00
[52] U.S. Cl. ...................................... 433/42; 433/80; 128/136
[58] Field of Search ..................... 433/42, 80; 128/136

[56] References Cited

U.S. PATENT DOCUMENTS 4,376,628  3/1983  Aardse .................................. 433/80
4,475,888  10/1984  Gores .................................... 433/42

Primary Examiner—Robert Peshock
Attorney, Agent, or Firm—Ford E. Smith; David L. Garrison

[57] ABSTRACT

A pair of U-shaped dentition trays are joined by a bendable bridging member that is reinforced by molded portions that function to maintain the trays biased apart and in tooth contact in a person's mouth.

5 Claims, 4 Drawing Figures

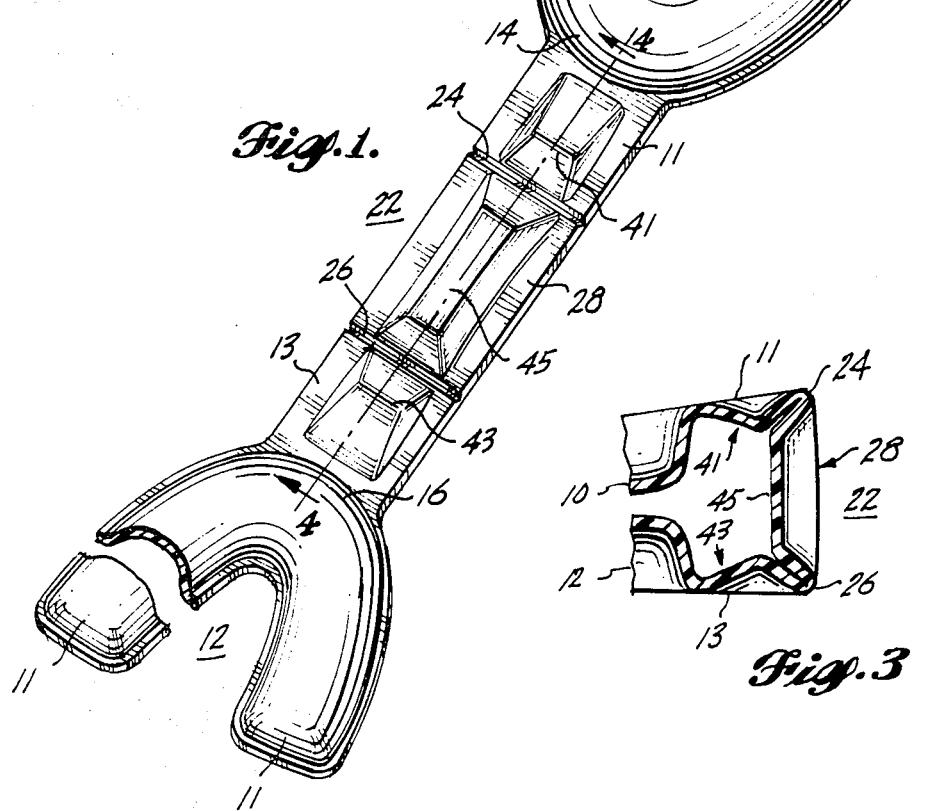

ANTERIORLY BRIDGED DENTAL TRAYS

RELATED APPLICATION

Ser. No. 369,783, Filed 04/19/82, Allowed 04/30/84.

SUMMARY OF THE INVENTION

In this invention a pair of U-shaped trays are joined anteriorly in mirror-like relation by a bridging member that is bendable or foldable into an arch that facilitates the trays being disposed bottom-to-bottom for insertion into a dental patient's mouth. By making an intermediate bridging member of a predetermined length greater than the combined thickness of the anterior portions of the trays, the apparatus assumes a wedge-like shape to facilitate placement in the mouth. A medical gel is deposited in the trays and is worked around and between the teeth in each tray by pumping action between his jaws produced by the patient. The device is usually manufactured by molding a thermoplastic foam sheet material for low cost production and to economically permit disposal after a single use.

A double tray dental apparatus as shown in this applicant's U.S. Pat. No. 3,536,069 has been extensively produced and used as a disposable device. In that instance the trays are normally arranged posterior-to-posterior with hinge means extending between the buccal exteriors of the trays. This application seeks to simplify production, to reduce cost, and to use less expensive material to produce a pair of trays. So far, as applicants know, their invention is structurally distinguishable from the dental tray of U.S. Pat. No. 3,955,281 in that the latter is unknown to be used in pairs or even so used to be joined anteriorly. A disposable device employing a posteriorly joined pair of trays produced by SULTAN DENTAL PRODUCTS of Englewood, N.J. is known but is to be distinguished by reason of the tray joinder elements extending between the posterior and not the anterior portions of paired trays.

DESCRIPTION OF THE DRAWINGS

FIG. 1 is a perspective view of the exterior of an anteriorly bridged pair of dental trays;

FIG. 2 is a side view of the pair of trays folded for insertion into a person's mouth;

FIG. 3 is a medial cross-section of the folded bridge;

FIG. 4 is a cross-section on line 4—4 of FIG. 1.

THE SPECIFICATIONS

In the preferred form of the invention, as shown in FIG. 1 of the drawings, a pair of arcuate dentition trays 10 and 12 are normally manufactured in an opposed relationship where their anterior portions 14 and 16 are respectively disposed in a mirror-like arrangement each looking toward the other.

Each tray is concavo-convex in cross-section to provide U-shaped troughs 18 and 20 that engage and cup the upper and lower teeth of a patient. These troughs receive a gel-like medication material pertinent to the topical treatment being conducted. Usually the material is a fluoride gel.

The arcuate trays 10 and 12 are joined by bridging member 22 which is usually formed of the same material as and integral with the trays. Bridging member 22 has a pair of spaced-apart fold or score lines 24 and 26 forming tray attached bridge portions 11 and 13, and the intermediate portion 28. The score lines facilitate folding the bridging member 22 to the disposition shown in FIGS. 2 and 3.

When the bridging member 22 has been folded to bring the convex posterior portions of the trays into the wedge-like juxtaposition of FIG. 2, the apparatus is ready for insertion into person's mouth.

The length of the bridge segment 28 is the distance B (see FIG. 2) between score line 24 and 26. When the bridge member 22 is folded at 24 and 26 as shown in FIG. 2, the anterior tray portions are not in contact whereas contact can occur between the more remote or posterior convex tray surfaces 32 and 34. The two trays are initially disposed wedge-like as shown and have a relatively lesser dimension A. In this fashion, introduction of the trays deeply into a person's mouth to encase the posterior molars is facilitated. When the mouth is then closed, tending to force the anterior portions of the trays together, bridge member 28 may spring slightly outward between score lines 24 and 26 to bias the tray anterior apart and tend to prevent displacement of the trays from the patient's forward or anterior jaw portions. The trays are also biased due to the inherent nature of the plastic material from which they are formed, to separate when not under compression. This ensures that the medication they contain is kept in intimate contact with the teeth.

The intermediate scores or fold lines 24, 26 usually localize the folding of bridge segments 11, 13 to an inward direction.

Each of the bridge portions 11 and 13 is stiffened by a hollow protrusion 41 and 43 provided during the molding or forming operation in the production of this dental apparatus. Likewise, the intermediate bridge portion 28 has hollow protrusion 45. In addition to stiffening, the bridging portions 41 and 43 and, particularly, intermediate portion 45, the portions 41 and 43 provide outward facing recesses that facilitate manually gripping the folded device for insertion and removal from the patient's mouth. Member 45 will tend to bow or hairpin when the patient's front teeth close toward each other but retains enough flexibility to spring back to the less bowed condition. In this way, member 45 biases the front or anterior portions of the trays apart tending, thusly, to keep the apparatus in place in the mouth.

The folded trays tend to return to the flat position due, in part, to the inherent elastic memory of the material. However, the configuration of the score lines 24 and 26 plus the contact and compression of the protrusions 41 and 43 with 45 aid greatly in this essential feature. The angulations of the sloped ends of bridge member 41 and 43 are designed to contact member 45 before the posteriors 32 and 34 come into contact. The additional force required to make tray ends 32 and 34 contact is stored in the compression and deformation of the parts 43, 45, and 41, and is released after insertion. We believe this to be unique and essential to the function of the tray.

The bridge is further designed to permit the trays to be fitted over the teeth in jaws which are misaligned or over the teeth in jaws with abnormal anterior-posterior relationships, e.g., the "Andy Gump" profile or the "Dick Tracy" profile. Trays joined at their posteriors do not permit this flexibility to fit.

It will be observed that when the bridging member 22 is folded, as in FIGS. 2 and 3, the protrusions 41 and 43 tend to abut and bolster the protrusion 45 of the intermediate bridge portion 28 thus forming a stiffened and relatively non-collapsible but springy and flexible arch of element 22.

It is intended that dental trays, according to this invention, be used only once and thereafter discarded. To that end it is desirable that this dental apparatus be formed or produced by a process which is high in volume, relative the attendant labor, and which employs readily available low cost material. High volume production is obtained by shaping the apparatus in molds using heat-moldable sheet material. An acceptable low cost sheet material is thermoplastic. Flexible polyurethane or polystyrene in fine-cell sheet form has performed very satisfactorily. The material, when molded, is smooth, semi-rigid, form retaining, and higly palatable. At the same time, it is suitable in its molded concavo-convex tray form to retain its integrity in a person's mouth despite pumping actions that may occur during treatment. Polyurethane foam has low water absorption characteristics and is suitably inert to the medical gel with which it is used. Such plastic materials do not react to the gel or breakdown or dissolve in the mouth. The preferred material is soft and sponge-like thus eliminating foam inserts previously used in dental trays as well as being comfortable in the patient's mouth. It is also inexpensive. This factor coupled to high volume, low cost molding ensures that the single used and throw-away disposal of the apparatus presents no economic hardship. Other plastic foams may also be useful.

Of course, a reusable form of apparatus according to this invention is conceivable. In such case, the molding of the opposed trays would be accomplished with more sophisticated materials capable of numerous uses, and adaptable to the cleansing and sterilizing techniques that would be required.

When the opposed arcuate troughs and bridge are being molded, the fold lines 24 and 26 may be provided by simply line squeezing or creasing without cutting the material during molding.

While the troughs 10 and 12 are shown herein as having closed ends for certain uses as, for example, in taking dental impressions or even when produced as mouth guards, the closed rear ends may be omitted.

It will be apparent that in this specification is set forth a complete description of a preferred form of the invention. Alternatives and modifications will readily come to mind to those skilled in the pertinent art. All such as under a liberal application of the doctrine of equivalents appropriate to the scope of this invention are intended to be covered by this patent.

PRIOR ART STATEMENT

Applicant is aware of the teachings of the referenced prior art which is considered not relevant or applicable singly or in combination of the claims in this patent application:

| References | | | | |
|---|---|---|---|---|
| 1 | 2,857,909 | 10/58 | Johnson | Cl. 178/136 |
| 2 | 3,416,527 | 12/68 | Hoef | 128/260 |
| 3 | 3,536,069 | 10/70 | Gores | 128/136 |
| 4 | 3,955,281 | 5/76 | Weitzman | 32/14B |
| 5 | 4,173,505 | 11/79 | Jacobs | 128/136X |
| 6 | 4,356,599 | 11/82 | Larson et al. | 24/16PB |
| 7 | 4,376,628 | 3/83 | Aardse | 433,42X |

A "Twintray" Disposable Fluoride Structure molded of a plastic foam material by SULTAN DENTAL PRODUCTS, Englewort, N.J. 07631, in which arcutate trays are flexibly joined at their posteriors is known to applicants.

What is claimed is:

1. In dental apparatus that comprises a pair of U-shaped dentition troughs, formed of soft, form-retaining plastic material, formed by a bridging member connected at each end between anterior upper edges of said troughs, the improvement, comprising:

said bridging member having a pair of fold-defining transverse creases, each crease being spaced from its joinder with an upper anterior edge of one of said troughs:

said transverse creases being spaced apart to define between them, a connector leg of a length such that when the troughs, through folding of said creases, are brought into bottom-to-bottom juxtaposed relation, the upper anterior ends of said troughs are maintained spaced apart a distance greater than the combined thickness of the posterior extremities of said troughs; and said connector leg being provided with means stiffening the same against significant bowing while subject to the pressures normally occurring when said troughs are brought into the described bottom-to-bottom juxtaposed relation as the apparatus is disposed for insertion into a person's mouth whereby the connector leg tends to bias the dentition troughs into intimate relation to the user's teeth while the apparatus is in place in the user's mouth.

2. The structure according to claim 1 in which the connector leg is stiffened by a hollow protrusion extending between its ends.

3. The structure according to claim 2 in which the hollow protrusion outstands from that side of the connector leg facing said dentition troughs.

4. The structure according to claim 1 in which each of the portions of the bridging member is stiffened by an integral concavo-convex protrusion.

5. The structure according to claim 4 in which the intermediate protrusion abuts with those on either side of it when the creases of the bridging member are folded.

* * * * *